United States Patent [19]

Towson et al.

[11] Patent Number: 5,663,361

[45] Date of Patent: Sep. 2, 1997

[54] PROCESS FOR PREPARING INTERMEDIATES TO FLORFENICOL

[75] Inventors: James C. Towson, Clinton; Dhiru B. Vashi, Princeton Junction, both of N.J.

[73] Assignee: Schering Corporation, Kenilworth, N.J.

[21] Appl. No.: 699,271

[22] Filed: Aug. 19, 1996

[51] Int. Cl.$^6$ .................................................. C07D 263/28
[52] U.S. Cl. ................................................... 548/233
[58] Field of Search ........................................ 548/233

[56] References Cited

U.S. PATENT DOCUMENTS

| | | | |
|---|---|---|---|
| 4,361,557 | 11/1982 | Nagabhushan | 424/226 |
| 4,876,352 | 10/1989 | Schumacher et al. | 548/232 |
| 5,382,673 | 1/1995 | Clark et al. | 548/239 |

Primary Examiner—Joseph McKane
Attorney, Agent, or Firm—Matthew Boxer; John J. Maitner

[57] ABSTRACT

A process for preparing a compound of formula I

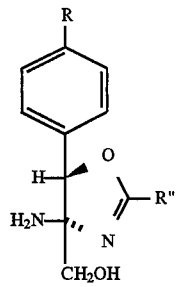

wherein R and R" are as described herein. Compounds of formula I are useful as intermediates in the preparation of florfenicol.

4 Claims, No Drawings

PROCESS FOR PREPARING INTERMEDIATES TO FLORFENICOL

FIELD OF THE INVENTION

The present invention relates to intermediates to florfenicol and to a novel process for preparing them.

BACKGROUND OF THE INVENTION

Florfenicol, also known as [R-(R*, S*)]-2,2-Dichloro-N-[1-(fluoromethyl)-2-hydroxy-2-[4-(methylsulfonyl)phenyl] ethyl]acetamide, is a broad spectrum antibacterial agent useful in the treatment of gram positive, gram negative and rickettsial infections as disclosed in U.S. Pat. No. 4,361,557 which is hereby incorporated by reference. The present invention relates to intermediates to florfenicol and to a novel process for preparing them. The intermediates described in the present specification can be used to prepare florfenicol as can be seen, for example, in U.S. Pat. No. 4,876,352, which is hereby incorporated by reference.

SUMMARY

In one embodiment, the present invention is directed toward a process for preparing a compound of formula I:

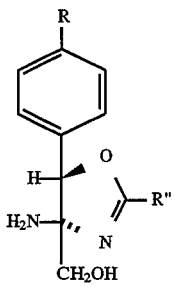

wherein R is H, $NO_2$, $CH_3S$, $CH_3SO_2$, or $C_4$ to $C_6$ alkyl; and R" is aryl, halo aryl, benzyl, substituted benzyl, $C_1$ to $C_6$ alkyl, $C_3$ to $C_7$ cycloalkyl, and haloalkyl, and the configuration of the oxazoline ring is 4R trans:

which comprises a) contacting a compound of formula II:

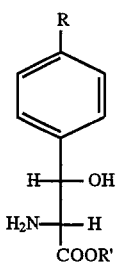

wherein R is as described above, and R' is H, $C_1$ to $C_6$ alkyl, $C_3$ to $C_7$ cycloalkyl, benzyl, substituted benzyl or aryl; with a reducing agent such as potassium borohydride, in a suitable reaction vessel, to obtain a compound of formula III:

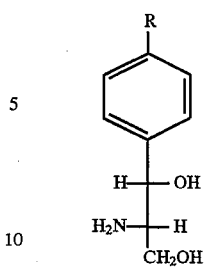

wherein R is as described above, and b) then in the same reaction vessel reacting a compound of formula III, with a compound of the formula IV:

$$R''-C\equiv N \qquad IV$$

wherein R" is as described above so as to obtain compound of the formula I.

The present invention has the advantage of being an efficient and economical process for preparing florfenicol, its analogs and oxazoline intermediates thereto.

DETAILED DESCRIPTION OF THE EMBODIMENTS

When utilized in the present specification and in the appended claims, the terms listed hereinbelow, unless otherwise indicated, are defined as follows:

The term "protic solvent" is intended to mean hydrogen-bonding solvent, as defined in James B. Hendrickson, Cram, Donald J., and Hammond, George S., *Organic Chemistry*, Mcgraw Hill Book Company, New York, N.Y., (1970), 1279 pp. The solvent should preferably, but not necessarily, be capable of precipitating oxazoline (I) out of solution. Such solvents include, but are not limited to, water, $C_1$ to $C_{10}$ alkanoic acids such as formic acid, acetic acid and the like, $C_1$ to $C_{10}$ alcohols such as methanol and ethanol and mixtures thereof, $C_2$ to $C_{10}$ dialcohols such as ethylene glycol and $C_1$ to $C_{10}$ trialcohols such as glycerin. Alternatively, the protic solvent can be admixed with any suitable cosolvent in order to effect precipitation of oxazoline compound (I). Such cosolvents can include other protic solvents which are miscible with the protic solvent such as $C_4$ to $C_{10}$ alkanes, aromatic solvents such as benzene, toluene, xylenes, halobenzenes such as chlorobenzene, and ethers such as diethylether, tert-butylmethylether, isopropylether and tetrahydrofuran, or mixtures of any of the above solvents or cosolvents.

The term "alkyl" means a straight or branched alkyl such as methyl, ethyl, propyl, or sec-butyl. Alternatively, the number of carbons in alkyl may be specified. For example, $C_1$ to $C_6$ alkyl means an alkyl as described above containing 1 to 6 carbon atoms. "Haloalkyl" means an "alkyl" as described above wherein one or more hydrogens are replaced by halo.

The term "aryl" means phenyl, or phenyl substituted by $C_1$ to $C_6$ alkyl or halo.

Substituted benzyl means benzyl substituted by $C_1$ to $C_6$ alkyl, or halo.

The term "halo" means fluoro, chloro, bromo, or iodo.

The term "halo aryl" means phenyl substituted by halo.

In the present specification,

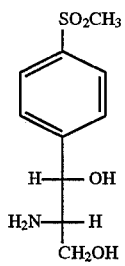

which is an aminodiol sulfone, is referred to as ADS.

The procedure for preparing the compounds of the invention can be represented as follows:

Formula Scheme

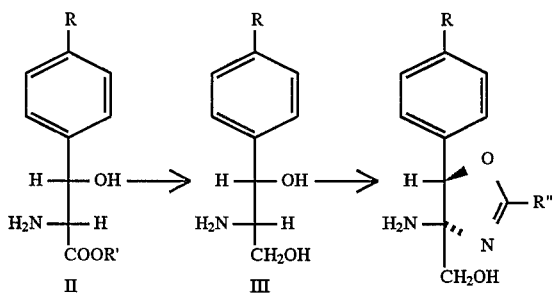

wherein R, R' and R" are as described herein.

With reference to the formula scheme above, a compound of formula I may be prepared as follows. A compound of formula II

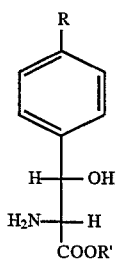

wherein R and R' are as described above is treated with a reducing agent such as $NaBH_4$, $Ca(BH_4)_2$, $LiBH_4$ or more preferably $KBH_4$ in a protic solvent such as ethanol, ethylene glycol, or more preferably methanol, at a temperature in the range of about 0° C. to about 30° C. more preferably room temperature for a period of about 2 to about 8 hours, more preferably about 4 hours to obtain a compound of formula III:

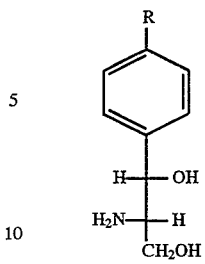

wherein R is as described above.

If, for example, in the reaction described just above, methanol is employed as the solvent in the reduction, it may be recovered by distillation for reuse in subsequent reactions. Removing methanol can also improve the yield of the compound of formula I.

In the same reaction vessel, the compound of formula III is contacted with a compound of formula IV,

R"—C≡N                    IV wherein R" is as described above, in the amount of about 1.1 to about 2.5 equivalents, preferably about 1.7 equivalents as compared to the compound of formula III.

Compounds of formula IV can be, for example, benzonitrile or dichloroacetonitrile. The reaction is run at a temperature between 25° C. and 115° C. depending upon the nitrile and the solvent employed. The reaction is run from about 6 hours to about 30 hours, preferably 18 hours. The reaction mixture is then cooled, for example, by the addition of cold water and worked up by conventional means such as filtration and washing to afford a compound of formula I. Preferably this step of the reaction is run at a pH in a range of about 6 to about 7.

An advantage of the present process is that it eliminates the need to isolate ADS, since both reaction steps are run in the same vessel.

Formation of the dichloromethyl oxazoline is preferred and the formation of the phenyl oxazoline is most preferred.

The serine ethyl ester, as shown below, is the preferred starting material of formula II.

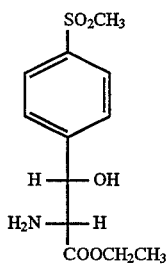

The following examples illustrate the present invention in a manner by which it can be practiced but, as such, should not be construed as limitations on the scope of the invention.

EXAMPLE 1

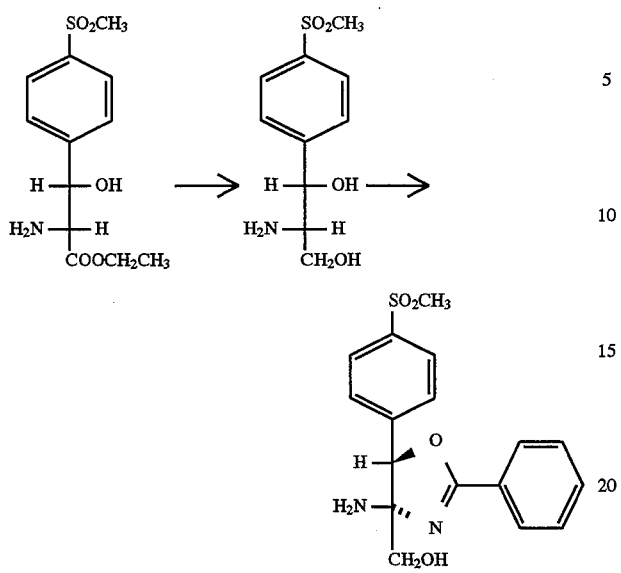

KBH$_4$ (1 g) is placed in about 40 mL of methanol. D-Threo p-methylsulfonyl phenyl serine ethyl ester (5 g) is added with stirring. The reduction to ADS is complete in several hours and can be monitored by HPLC. When the reaction is complete, 20 mL of glycerin is added to destroy any excess reducing agent and methanol is removed by distillation. After the methanol has been removed, the resulting mixture is heated to 105° C. and benzonitrile (3.1 mL) is added while continuing heating for about 18 hours. Formation of the desired oxazoline can be monitored by HPLC. The reaction is cooled to room temperature and worked up by addition of cold water, filtration of the resulting solids, washing of the solids with methanol then drying under vacuum. The yield is about 4.7 g (81%) of material that is identical to an authentic sample of the phenyl oxazoline.

EXAMPLE 2

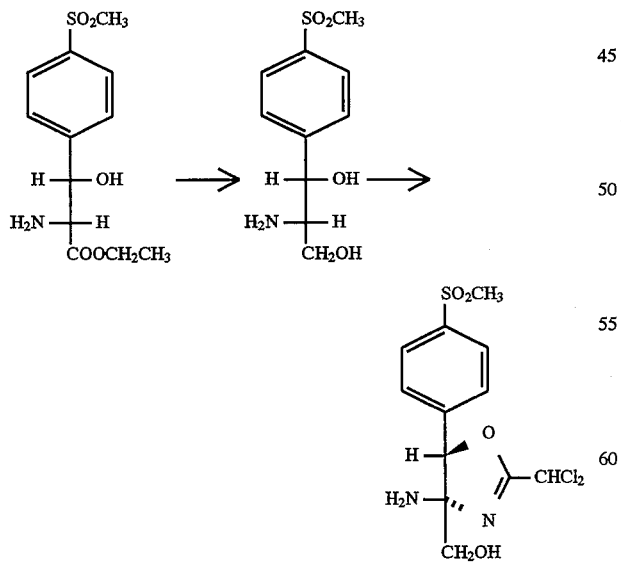

KBH$_4$ (1 g) is placed in about 40 mL of methanol. D-Threo p-methylsulfonylphenyl serine ethyl ester (5 g) is added with stirring. The reduction to ADS is complete in several hours and can be monitored by HPLC. When the reaction is complete, 20 mL of glycerin is added to destroy any excess reducing agent and methanol is removed by distillation. After the methanol has been removed, the resulting mixture is acidified to a pH of about 6 to 7 with H$_2$SO$_4$ and dichloroacetonitrile (2.4 g) is added. The reaction is stirred at 50° C. for about 18 hours. Formation of the desired oxazoline can be monitored by HPLC. The reaction is cooled to room temperature and worked up by filtration of the solids, washing of the solids with isopropanol and 2% NaHCO$_3$ then drying under vacuum. The yield is about 3.8 g (65%) of material that is identical to an authentic sample of the dichloro oxazoline.

THE STARTING MATERIALS

The starting materials of formula (II) and (IV) are known to those skilled in the art.

What is claimed is:

1. A process for preparing a compound of formula (I):

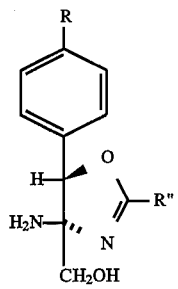

wherein R is H, NO$_2$, CH$_3$S, CH$_3$SO$_2$, or C$_4$ to C$_6$ alkyl; and R" is aryl, halo aryl, benzyl, substituted benzyl, C$_1$ to C$_6$ alkyl, C$_3$ to C$_7$ cycloalkyl, and haloalkyl, and the configuration of the oxazoline ring is 4R trans:

which comprises a) contacting a compound of formula II:

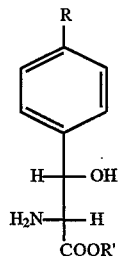

wherein R is as described above, and R' is H, C$_1$ to C$_6$ alkyl, C$_3$ to C$_7$ cycloalkyl, benzyl, substituted benzyl, or aryl; with a reducing agent, in a suitable reaction vessel, to obtain a compound of formula III:

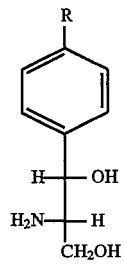

wherein R is as described above, and b.) then in the same reaction vessel reacting a compound of formula III, with a compound of the formula IV:

R"—C≡N  IV
to obtain a compound of the formula I.
2. A process according to claim 1 wherein the reducing agent is potassium borohydride.
3. A process according to claim 1 wherein the compound of formula I that is formed is:
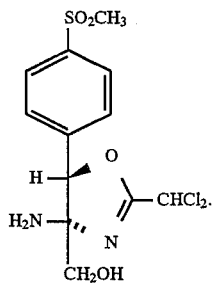
4. A process according to claim 1 wherein the compound of formula I that is formed is:
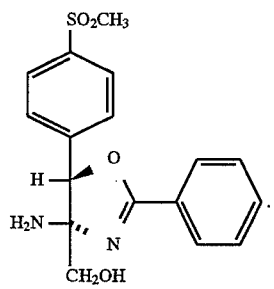
* * * * *

UNITED STATES PATENT AND TRADEMARK OFFICE
CERTIFICATE OF CORRECTION

PATENT NO : 5,663,361
DATED : September 2, 1997
INVENTOR(S): J. Towson, et al

It is certified that error appears in the above-identified patent and that said Letters Patent is hereby corrected as shown below:

In the Abstract: Change the figure to:

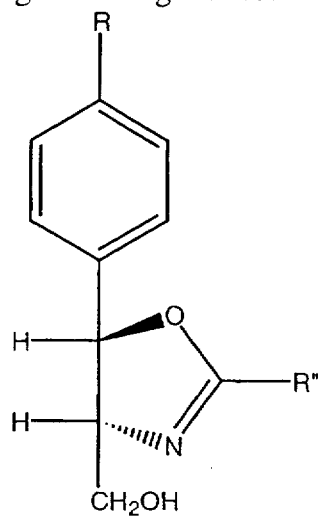

UNITED STATES PATENT AND TRADEMARK OFFICE
CERTIFICATE OF CORRECTION

PATENT NO : 5,663,361
DATED : September 2, 1997
INVENTOR(S): J. Towson, et al

It is certified that error appears in the above-identified patent and that said Letters Patent is hereby corrected as shown below:

In col. 1, lines 30-40, change the figure to:

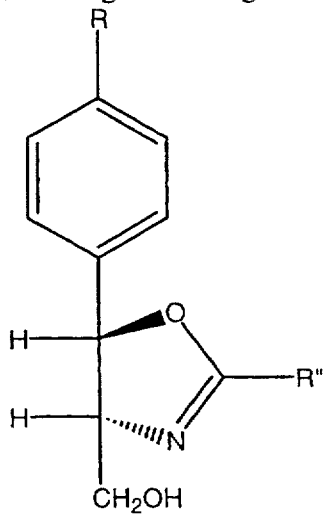

UNITED STATES PATENT AND TRADEMARK OFFICE
CERTIFICATE OF CORRECTION

PATENT NO : 5,663,361
DATED : September 2, 1997
INVENTOR(S): J. Towson, et al

It is certified that error appears in the above-identified patent and that said Letters Patent is hereby corrected as shown below:

In col. 3, lines 25-35, change the figure to:

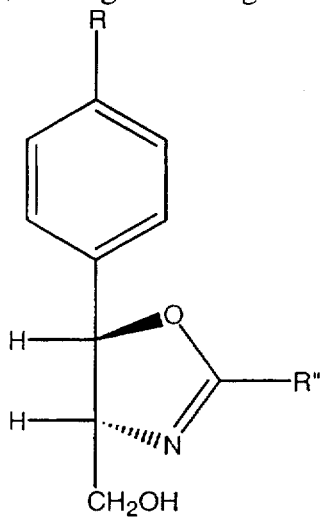

UNITED STATES PATENT AND TRADEMARK OFFICE
CERTIFICATE OF CORRECTION

PATENT NO : 5,663,361
DATED : September 2, 1997
INVENTOR(S): J. Towson, et al

It is certified that error appears in the above-identified patent and that said Letters Patent is hereby corrected as shown below:

In Example I, col. 5, lines 13-24, change the figure to:

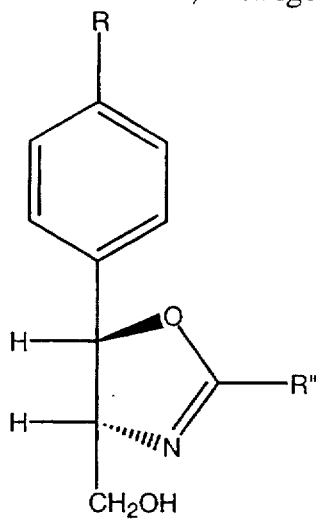

UNITED STATES PATENT AND TRADEMARK OFFICE
CERTIFICATE OF CORRECTION

PATENT NO : 5,663,361
DATED : September 2, 1997
INVENTOR(S): J. Towson, et al

It is certified that error appears in the above-identified patent and that said Letters Patent is hereby corrected as shown below:

In Example II, col. 5, lines 53-65, change the figure to:

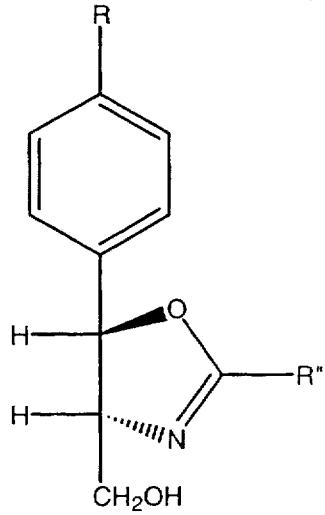

UNITED STATES PATENT AND TRADEMARK OFFICE
CERTIFICATE OF CORRECTION

PATENT NO : 5,663,361
DATED : September 2, 1997
INVENTOR(S): J. Towson, et al

It is certified that error appears in the above-identified patent and that said Letters Patent is hereby corrected as shown below:

In Claim 1, col. 6, lines 22-32, change the figure to:

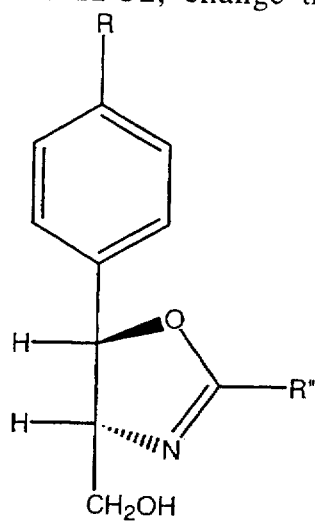

UNITED STATES PATENT AND TRADEMARK OFFICE
CERTIFICATE OF CORRECTION

PATENT NO : 5,663,361
DATED : September 2, 1997
INVENTOR(S): J. Towson, et al

It is certified that error appears in the above-identified patent and that said Letters Patent is hereby corrected as shown below:

In Claim 3, col. 7, lines 8-17, change the figure to:

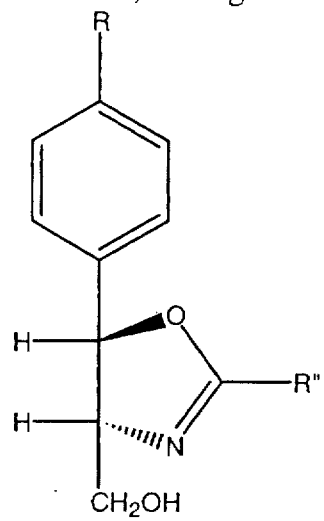

UNITED STATES PATENT AND TRADEMARK OFFICE
CERTIFICATE OF CORRECTION

PATENT NO : 5,663,361
DATED : September 2, 1997
INVENTOR(S): J.Towson, et al

It is certified that error appears in the above-identified patent and that said Letters Patent is hereby corrected as shown below:

In Claim 4, col. 8, lines 4-17, change the figure to:

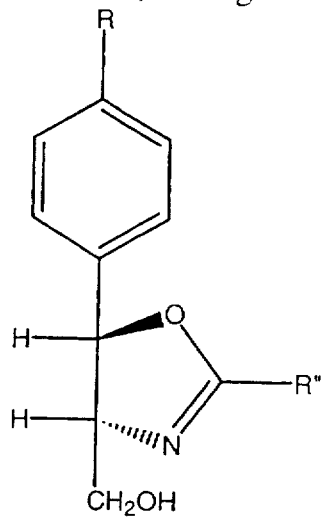

Signed and Sealed this

Thirtieth Day of November, 1999

Q. TODD DICKINSON

*Attest:*

*Attesting Officer*      *Acting Commissioner of Patents and Trademarks*